United States Patent [19]

Florindez et al.

[11] 4,307,740

[45] Dec. 29, 1981

[54] TOOTH CLEANER

[76] Inventors: Augusto Florindez, 13029 Ocaso Ave., La Mirada, Calif. 90638; Robert L. Gaylord, 17807 Beshire, Artesia, Calif. 90701

[21] Appl. No.: 194,165

[22] Filed: Oct. 6, 1980

[51] Int. Cl.³ .............................................. A61C 15/00
[52] U.S. Cl. .................................. 132/92 R; 132/11 R
[58] Field of Search .................. 132/89, 90, 91, 92 R, 132/92 A, 141, 11 R

[56] References Cited

U.S. PATENT DOCUMENTS

| | | | |
|---|---|---|---|
| 3,534,745 | 10/1970 | Waters | 132/92 R |
| 3,667,483 | 6/1972 | McCabe | 132/92 A |
| 3,799,177 | 3/1974 | Bragg | 132/92 R |
| 3,847,167 | 11/1974 | Brien | 132/92 R |

Primary Examiner—Robert Peshock
Attorney, Agent, or Firm—Whann & McManigal

[57] ABSTRACT

A tooth cleaning, polishing and gum massaging device having a pair of fingers attached to extend on opposite sides of the teeth to be cleaned and supporting a cleaning thread which extends from one finger to the other and between the teeth, the surface of which are to be cleaned. There is an operating element which causes the fingers to move up and down relative to the teeth and for moving the cleaning thread back and forth in sideward directions, thus moving the cleaning thread up and down relative to the in-between surfaces of the teeth and moving the thread sidewardly, thus moving the cleaning thread in a plurality of directions.

8 Claims, 10 Drawing Figures

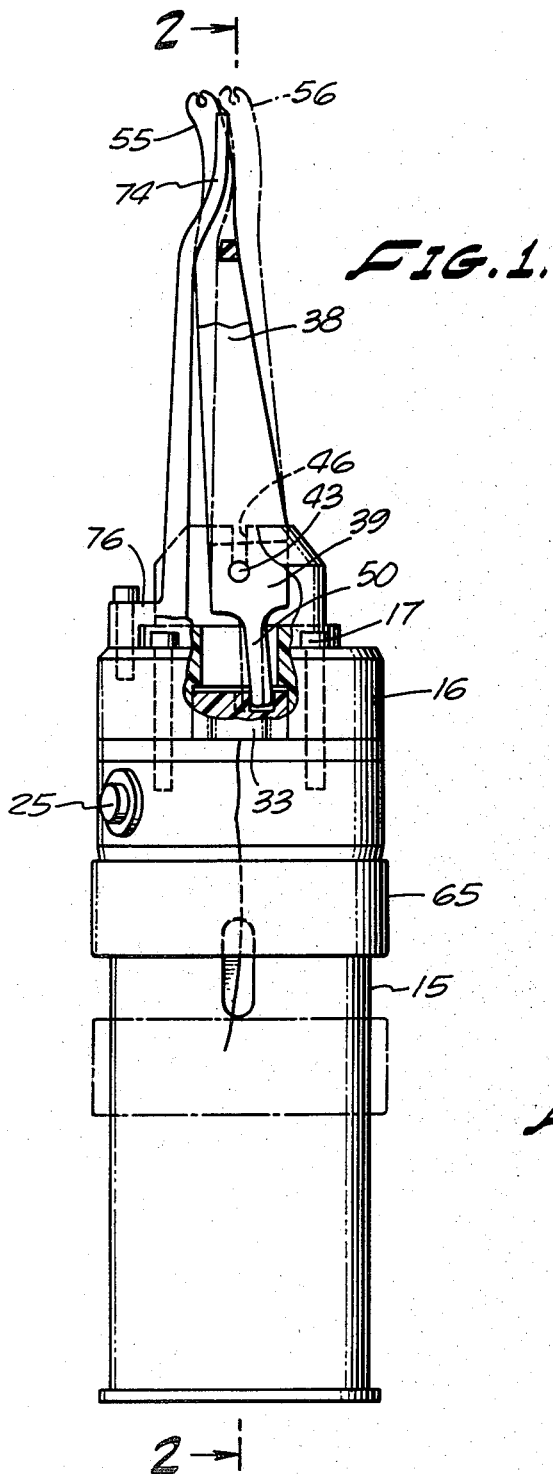
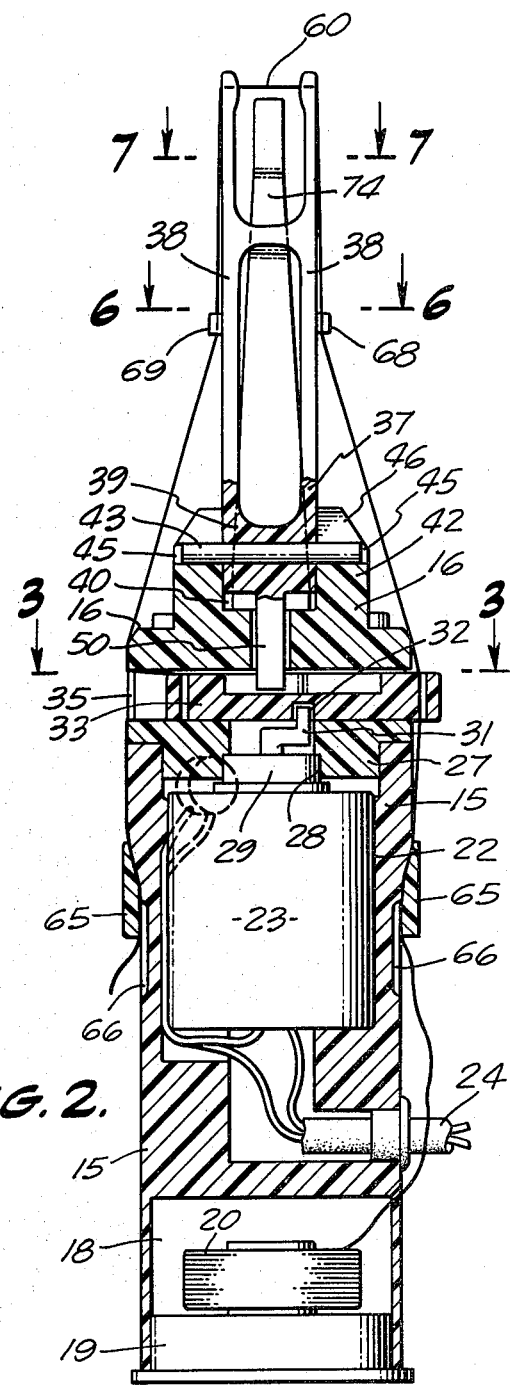

TOOTH CLEANER

Our invention relates to a tooth cleaning and polishing and gum massaging device for gently and thoroughly cleaning the between the teeth surfaces. A dental floss is commonly used for this purpose but it is difficult to do a through job because of the difficulty in holding the dental floss in a proper position and moving the floss in such a way that all the between the teeth surfaces can be engaged.

It is an object of our invention to provide a device of the character described in which there is a pair of fingers supporting the dental floss between them, the pair of fingers being capable of being positioned on opposite sides of the teeth with the dental floss extending originally between the teeth, the fingers being moved vertically and the dental floss being moved horizontally.

It is an object of our invention to provide a cleaning, polishing and massaging device which is motorized and movement of the parts is accomplished by pressing a button which energizes the motor.

It is an object of our invention to provide a device of the character described in which both the horizontal movement of the thread relative to the fingers is accomplished simultaneously, the operator merely holding the device in a position where the fingers and the dental floss is automatically moved.

It is an object of our invention to provide a device of the character described in which the floss is held taut so that the device can be moved in order to cause the dental floss to engage the surfaces of the teeth so that thorough cleaning and polishing can be accomplished in a minimum of time.

It is a still further object of our invention to provide a device of the character described in which the parts are removable for easy convenient cleaning. Other objects and advantages of our invention will be made evident during the course of the following detailed description of preferred embodiment of our invention.

Referring to the drawings which are made on an enlarged scale in order to better show the details, FIG. 1 is an elevational view partly cut away to show the means whereby the fingers are moved by motor means between full line and dotted line positions.

FIG. 2 is a vertical sectional view taken along the line 2—2 showing the thread spool chamber, the motor chamber and the oscillating means whereby the fingers are moved vertically and the thread is moved horizontally.

Figure 3:
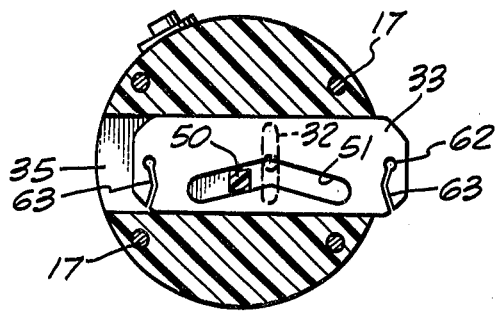
FIG. 3 is a sectional view taken on the line 3—3 with the operating member shown in its position at the end of an operating stroke in one direction.

Referring now to the drawings in detail, our invention provides a support structure having a body 15 and a head 16, the parts being secured together by screws 17.

The body is cylindrical and acts as a handle. In the lower part of the body is a thread or floss spool chamber 18 closed by a plug 19, in which chamber is the spool of floss 20.

Also formed in the body is a motor chamber 22 which houses a motor 23, which receives electricity through the cord 24. There is a manually operable switch 25 conveniently located so that the operator can press the switch button and energize the motor 23 in order to put the device into operation.

The head 16 has a projection 27 which closes the motor chamber. The projection 27 has a centralized opening 28 into which there extends a shoulder 29 which centralizes the motor.

The motor has a crank 31 which extends into a horizontal slot 32 of an operating member or oscillating bar 33. When the crank is operated by energizing the motor, the oscillating bar 33 moves between the positions shown in FIGS. 3, 4 and 5. The oscillating bar as shown is rectangular in cross-section and is positioned in and moves in a horizontal slot 35 formed in the head 16.

Mounted on the head 16 is a thread support 37 which has two fingers 38 projecting from a base 39 which fits into a socket formed formed in the enlargement 42 on the head 16.

The thread support pivots around a shaft 43 which extends through the base with the ends thereof positioned in openings 45 formed in the enlargement 42, the openings 45 having entrance slots 46 whereby thread support can be easily removed and installed, this being easily accomplished by raising or lowering the thread or dental floss support relative to the enlargement 42.

This simple arrangement makes the thread support readily removable for cleaning.

The thread support is associated with the operating bar by pin and cam means which causes the thread support to be moved back and forth. The numeral 50 indicates the downwardly extending pin, the lower end of which extends into a cam slot 51, which slot has two positions formed at angles so that as the oscillating bar 33 moves back and forth the pin 50 is caused to oscillate from the position shown in FIG. 3 thru the position shown in FIG. 4 and into the position shown in FIG. 5. This horizontal movement causes the thread supporting member to oscillate on the pivot shaft 43 causing the ends of the fingers, as shown in FIG. 1, to move from full position 55 to dotted line position 56, thus producing the vertical oscillating movement of the finger ends.

Figure 8:
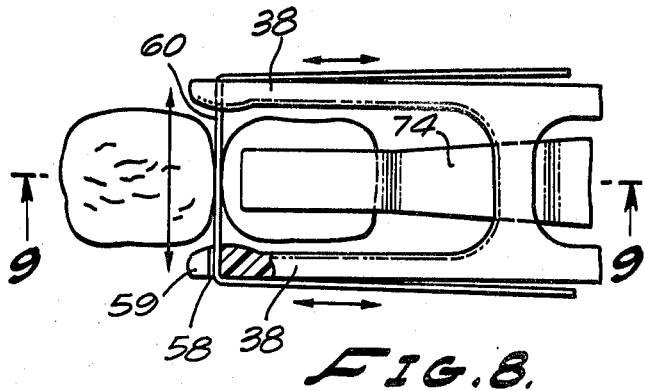
FIG. 8 is a fragmentary view showing the fingers positioned to hold the floss between the teeth, the view looking in a downward direction showing the fingers extending on opposite sides of the teeth.
Figure 9:
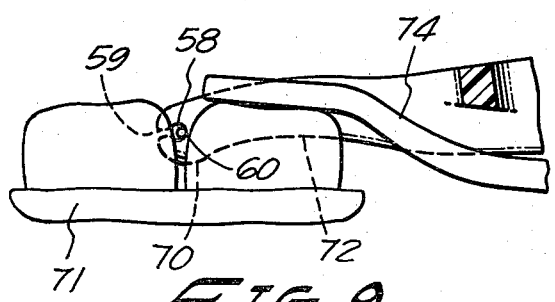
FIG. 9 is a fragmentary sectional view looking in a horizontal position showing the fingers in a raised position.
Figure 7:
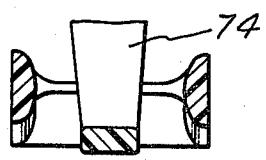
FIG. 7 is a cross-sectional view taken on line 7—7 of FIG. 2.
Figure 10:
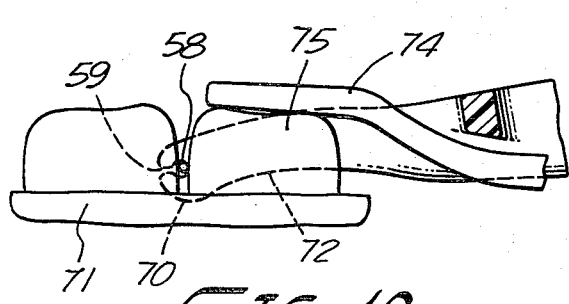
FIG. 10 is a view similar to FIG. 9 showing the fingers in a lowered position.
Figure 6:
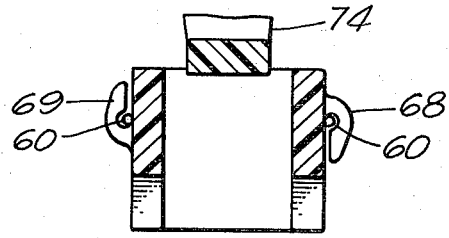
FIG. 6 is a sectional view taken on the line 6—6 showing the finger guides mounted on the fingers.

When the device is in use, the fingers 33 are positioned on opposite sides of the teeth as shown in FIG. 8 and when the ends of the fingers are oscillated the fingers move from a raised position as shown in FIG. 9 into a lowered position as shown in FIG. 10.

The ends of the fingers have thread or floss openings 58 having entrance slots 59 for easy installation of the floss. As shown in FIG. 8 a section 60 of the dental floss is held taut between the ends of the fingers.

Figure 4:
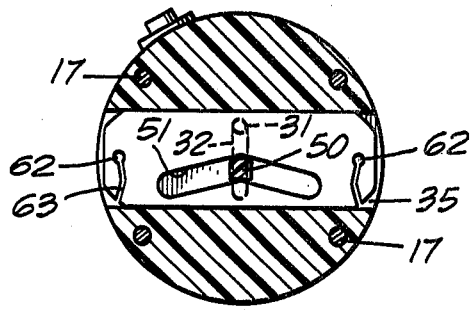
FIG. 4 is a similar sectional view showing the operating member in a central position.
Figure 5:
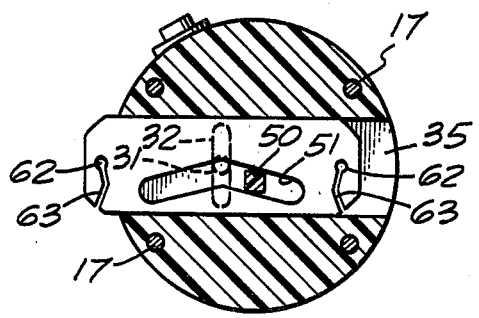
FIG. 5 is a similar sectional view showing the operating member at the end of its stroke opposite from the position shown in FIG. 3.

As shown in FIGS. 3 to 5 the ends of the oscillating bar 33 have thread or floss openings 62 with entrance slots 63, these openings 62 being positioned in opposite ends of the bar 33.

The thread or floss extends from the spool chamber 20 along the body and within the lock means in the form of a lock ring 65, and having recesses 66 to provide space when the ring 65 is in a lowered position. When the threading operation has been completed the ring 65 is returned to its thread engaging position as shown in FIG. 2.

The floss is then extended into the opening 62, the bar 33 being in the position shown in FIG. 3. The thread is then extended through the guide 68, then through the openings 58 in the ends of the fingers and then downwardly along the opposite finger and through the guide 69.

The oscillating bar 33 is then moved from the position shown in FIG. 3 into the position shown in FIG. 5, and the thread or floss is then extended through the left thread opening 62 as shown in FIG. 5, the bar 33 having been moved from the position shown in FIG. 3 into the position shown in FIG. 5. The thread is then extended downwardly and between the ring 65 and the wall of the body, the ring at this time being in lowered position.

The operator then holds the dental floss from moving on the right hand side of the device as shown in FIG. 2; and the operator pulls tightly on the end of the floss in order to tighten and hold the floss taut in order that section 60 of the floss as shown in FIG. 8, will be stretched between the ends of the fingers. The operator then pushes the clamping ring 65 upwardly in the position shown in 62 and the floss is then being held under proper tension and in working position.

The operation of the device is as previously suggested, the motor being set into operation by closing the switch 25. This causes the crank 31 to oscillate the bar 33 which moves the pin 50 back and forth in order to oscillate the fingers 38. The second movement which occurs is that of oscillating the thread or floss. When the bar is in the position shown in FIG. 2, the left end of the bar is within the slot 35 and the thread has been pulled into the slot and causes the portion of the floss above the bar to be moved in a direction that the section of the floss extending between the fingers as indicated at 60 moves in a leftward direction in FIG. 2.

When the bar moves to the position shown in FIG. 5 the floss is pulled into the right hand end of the slot 35, thus causing the floss to move in the opposite direction. Because of the relationship of the floss extending through opposite ends of the bar 33, there is a compensating effect and the floss is held taut at all times.

During this operation the ends of the fingers are moved between the positions shown in FIGS. 9 and 10. It will be noted that the ends of the fingers have bulges 70 which, when the fingers are in their lowered position, engage the gums 71 and perform a massaging effect. Also it will be noted that the ends of the fingers are curved as indicated at 72 in order to give clearance so that the fingers, other than at 70, will not engage the gums.

In order to prevent the fingers from being accidentally placed in too low a position, a depth gage 74 is provided. This depth gage is secured to the thread holder at 76 and the end portion being mounted between the ends of the fingers is capable of engaging the top surface of the teeth 75 as shown in FIGS. 8, 9 and 10. The depth gage is made flexible so that, although the lower position of the ends of the fingers are positioned properly by exerting a little pressure in a vertical direction, the depth gage will flex and permit the ends of the fingers to be moved a little lower.

When floss 60 has been worn, a new section may readily be brought into operating position by moving the clamp ring 65 downwardly and at that time shifting the thread to bring a new unused portion 60 between the fingers 33.

We claim:

1. A cleaning and polishing device for cleaning and polishing the in-between surface between teeth having a body serving as a handle, the combination including:
   a. a cleaning thread support having fingers attached to extend on opposite sides of the teeth to be cleaned,
   b. a cleaning thread having a portion extending between said fingers,
   c. means for moving said fingers up and down relative to said body and to the teeth, thus moving the cleaning thread on the in-between surface of the teeth in an up and down direction, and
   d. means for moving said cleaning thread back and forth in a sideward direction between the fingers thus moving the thread back and forth in contact with the in-between surfaces of the teeth.

2. A combination as defined in claim 1 in which the end portions of said fingers have gum massaging portions for engaging and massaging the gums.

3. A combination as defined in claim 1, which includes motor means for simultaneously moving said fingers up and down relative to said handle and moving said cleaning thread horizontally back and forth.

4. A combination as defined in claim 1 in which said fingers are a part of a thread support pivoted to the support structure of said device to swing back and forth, operating member carried by said support structure attached to oscillate back and forth, and a pin and cam means cooperating between said thread support and said operating member for swinging said thread support back and forth in order to move the thread supporting fingers.

5. A combination as defined in claim 1 in which the support structure of said device has an operating member which moves back and forth in a sidewardly direction, the operating member having two ends which alternately are projected from the supporting structure when said operating member moves back and forth, and in which said cleaning thread is engaged by said operating member to cause it to oscillate back and forth, thus causing the portion of the cleaning thread positioned between said fingers to move back and forth in a sideward direction during the cleaning and polishing operation.

6. A combination as defined in claim 1 in which there is a means for holding said cleaning thread taut during its movement back and forth.

7. A combination as defined in claim 2 which includes a depth gage adapted to engage the end of the tooth for properly positioning the fingers to move up and down relative to the teeth and to bring the gum massaging portion into engagement with the gums for massaging the gums.

8. A combination as defined in claim 7 in which the depth gage is flexible in order to provide adjustability to the position in which the fingers are positioned.

* * * * *